United States Patent
Ueda et al.

(10) Patent No.: US 9,983,166 B2
(45) Date of Patent: May 29, 2018

(54) NITROGEN OXIDE RESPONSIVE ELEMENT AND METHOD FOR PRODUCING SAME

(71) Applicants: JAPAN FINE CERAMICS CENTER, Nagoya-shi, Aichi (JP); TOYOTA JIDOSHA KABUSHIKI KAISHA, Toyota-shi, Aichi-ken (JP)

(72) Inventors: Taro Ueda, Nishisonogi-gun (JP); Hajime Okawa, Seto (JP); Masaya Suzuki, Nagoya (JP); Takafumi Ogawa, Nagoya (JP); Seiji Takahashi, Ichinomiya (JP); Toyoharu Kaneko, Susono (JP); Keiichiro Aoki, Nagaizumi-cho (JP)

(73) Assignees: JAPAN FINE CERAMICS CENTER, Aichi (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 83 days.

(21) Appl. No.: 14/943,740

(22) Filed: Nov. 17, 2015

(65) Prior Publication Data

US 2016/0139074 A1    May 19, 2016

(30) Foreign Application Priority Data

Nov. 17, 2014 (JP) .................................. 2014/233083

(51) Int. Cl.
  *G01N 27/407* (2006.01)
  *G01N 27/41* (2006.01)
  (Continued)

(52) U.S. Cl.
  CPC .......... *G01N 27/4075* (2013.01); *C30B 7/06* (2013.01); *C30B 29/22* (2013.01); *G01N 27/41* (2013.01);
  (Continued)

(58) Field of Classification Search
  CPC .. B01D 53/32; B01D 53/326; B01D 53/9422; B01D 53/9409; B01D 2255/40;
  (Continued)

(56) References Cited

U.S. PATENT DOCUMENTS 5,861,092 A    1/1999 Kiyota et al.
6,019,881 A    2/2000 Kurosawa et al.
(Continued)

FOREIGN PATENT DOCUMENTS

CN    1152352 A    6/1997
CN    1212369 A    3/1999
(Continued)

OTHER PUBLICATIONS

Mar. 14, 2017 Office Action issued in European Patent Applicaton No. 15 195 18.5.
(Continued)

*Primary Examiner* — Gurpreet Kaur
(74) *Attorney, Agent, or Firm* — Oliff PLC

(57) ABSTRACT

The present specification provides a NOx responsive element suitable for directly sensing NOx. The NOx responsive element an oxygen ion conductive layer has a first electrode layer having a nitrogen oxide decomposition catalyst phase composed of perovskite-type oxide, being in contact with the oxygen ion conductive layer, and being exposed to NOx, and a second electrode layer opposing the first electrode layer across the oxygen ion conductive layer. The nitrogen oxide decomposition catalyst phase has a nitrogen oxide adsorption stabilizing surface on its surface exposed to nitrogen oxide.

3 Claims, 9 Drawing Sheets

(51) Int. Cl.
*G01N 33/00* (2006.01)
*C30B 29/22* (2006.01)
*C30B 7/06* (2006.01)

(52) U.S. Cl.
CPC ........ *G01N 33/0037* (2013.01); *Y02A 50/245* (2018.01)

(58) Field of Classification Search
CPC ...... B01D 2255/402; B01D 2255/2063; B01D 53/402; B01D 53/2063; G01N 33/0037; G01N 27/04075; B01J 23/34; B01J 23/002
See application file for complete search history.

(56) References Cited

U.S. PATENT DOCUMENTS

| | | | | |
|---|---|---|---|---|
| 2010/0092829 | A1* | 4/2010 | Fontaine | C01F 17/0018 429/489 |
| 2016/0123920 | A1* | 5/2016 | Ueda | B01D 53/32 205/781 |
| 2016/0280674 | A1* | 9/2016 | Backharicoult | C07D 301/04 |

FOREIGN PATENT DOCUMENTS

| | | |
|---|---|---|
| JP | H07-265651 A | 10/1995 |
| JP | 2006-289248 A | 10/2006 |
| JP | 2010-122187 A | 6/2010 |
| JP | 2010-261855 A | 11/2010 |
| JP | 4721098 B2 | 7/2011 |
| JP | 2014-171919 A | 9/2014 |

OTHER PUBLICATIONS

Mar. 18, 2016 Extended Search Report issued in European Patent Application No. 15195018.5.

Ueda et al., "Amperometric-type NOx sensor based on YSZ electrolyte and La-based perovskite-type oxide sensing electrode," Journal of the Ceramic Society of Japan, vol. 118, No. 3, 2010, pp. 180-183.

Ueda et al., "Zirconia-based amperometric sensor using La—Sr-based perovskite-type oxide sensing electrode for letection of NO2," Electrochemistry Communications, vol. 11, 2009, pp. 1654-1656.

Piskunov et al. "Electronic structure and thermodynamic stability of LaMnO3 and La1-xSrxMnO3 (001) surfaces: Ab initio calculations" Physical Review. B, vol. 78, 2008, pp. 121406-1 through 121406-4.

Hamedani et al., "Fabrication of gradient porous LSM cathode by optimizing deposition parameters in ultrasonic spray pyrolysis" Materials Science and Engineering B, vol. 153, 2008, pp. 1-9.

Maity et al., "Phase, morphology and core-level electron spectroscopy of nano-sized La0.65Sr0.35MnO3 powders prepared by solution combustion synthesis," Journal of Physics and Chemistry of Solids, vol. 74, 2013, pp. 315-321.

Oct. 25, 2016 Office Action issued in Japanese Patent Application No. 2014-233083.

Nov. 7, 2017 Office Action issued in Chinese Patent Application No. 201510789103.5.

Hao, Zeng-Chuan et all. "Investigation on Impedencemetric-type NO2 Sensor Based on La0.75Sr0.25Mn0.5Co0.5O3-δ Sensing Electrode". Journal of Inorganic Materials, vol. 26, No. 5, pp. 523-528, 2011.

* cited by examiner

NITROGEN OXIDE RESPONSIVE ELEMENT AND METHOD FOR PRODUCING SAME

CROSS REFERENCE TO RELATED APPLICATIONS

This application is related to Japanese Patent Application No. 2014-233083 filed on Nov. 17, 2014 and claims priority to the Japanese application entire contents of which are incorporated by reference herein.

TECHNICAL FIELD

The present specification relates to a nitrogen oxide responsive element and a method for producing the same.

DESCRIPTION OF RELATED ART

Nitrogen oxide (hereinafter also merely referred to as NOx) such as nitrogen monoxide or nitrogen dioxide contained in exhaust and the like of vehicles has been decomposed by a NOx decomposition device to suppress emission thereof. In order to effectively operate the NOx decomposition device, it is important to sense the NOx concentration in exhaust with high accuracy.

A conventional NOx sensor is based on a method in which introduced exhaust is burned in a first chamber to remove combustible components, and remaining oxygen is thereafter removed by an oxygen pump, remaining gas is introduced into a second chamber to decompose NOx into nitrogen and oxygen, and oxygen is pumped, and the NOx concentration is detected from an obtained current.

Patent Document 1: Japanese Patent Application Laid-open No. 2010-122187

BRIEF SUMMARY OF INVENTION

However, in this kind of NOx sensor, a complicated structure and a multistage control are required, and in the meanwhile, the technique of directly sensing NOx is not satisfactory enough, and excellent NOx responsive element has not yet been provided.

The present specification provides a NOx responsive element suitable for directly sensing NOx and a method for producing the same.

The inventors of the present teaching used a LaSrMn-based perovskite material as a material for sensing NOx and conducted studies on the improvement in sensing sensitivity and NOx selective sensing ability to oxygen in a sensing layer composed of this perovskite material. The inventors of the present teaching found that some surface structures in the crystal structure of ceramics such as perovskite-type oxide are different in NOx adsorption characteristics and further found that the NOx responsive sensitivity and the NOx selectivity can be improved by exposing the termination surface which most stabilizes the adsorption of NOx as a surface exposed to NOx, for example. In addition, the inventors of the present teaching found that an adsorption stabilizing surface which can stabilize adsorption of NOx can be formed into a sensing layer, and the NOx detection sensitivity can be improved by the surface. The inventors of the present teaching further found that the NOx selective detection ability can be improved by controlling the density of the sensing layer. Based on these findings, the following disclosure is provided.

(1). A nitrogen oxide responsive element comprising:
an oxygen ion conductive layer;
a first electrode layer having a nitrogen oxide decomposition catalyst phase composed of perovskite-type oxide, being in contact with the oxygen ion conductive layer, and being exposed to NOx, and
a second electrode layer opposing the first electrode layer across the oxygen ion conductive layer,
wherein the nitrogen oxide decomposition catalyst phase has a surface exposed to nitrogen oxide and the surface includes a nitrogen oxide adsorption stabilizing surface.

(2) The element according to claim 1, wherein
the perovskite-type oxide is LaSrMn-based perovskite oxide, and
the nitrogen oxide adsorption stabilizing surface is an $MnO_2$ surface.

(3) The element according to (1) or (2), wherein
the first electrode layer is denser on a side of the oxygen ion conductive layer.

(4) The element according to any one of (1) to (3), wherein
particle growth of the perovskite-type oxide is suppressed more on a side exposed to nitrogen oxide in the first electrode layer.

(5) A method for producing the nitrogen oxide responsive element according to claim 1, comprising;
forming the first electrode layer having the nitrogen oxide decomposition catalyst phase composed of perovskite-type oxide on a layer composed of an oxygen ion conductive material,
wherein the first electrode layer forming is performed so as to form the NOx adsorption stabilizing surface on the surface exposed to nitrogen oxide.

(6) The production method according to (5), wherein
the first electrode layer forming includes firing a raw material of LaSrMn-based perovskite-type oxide under oxygen rich atmosphere to form the first electrode layer.

(7) The production method according to (5) or (6), wherein
the first electrode layer forming step includes forming the first electrode layer so as to be denser on a side of the oxygen ion conductive layer.

(8) The production method according to any one of (5) to (7), wherein
the first electrode layer forming step includes forming the first electrode layer so that particle growth of the perovskite-type oxide is suppressed more on the surface exposed to nitrogen oxide (9) A nitrogen oxide sensor comprising the element according to any one of (1) to (4).

DETAILED DESCRIPTION OF INVENTION

The disclosure of the present specification relates to a NOx responsive element, a method for producing the same, a NOx sensor, and the like. The NOx responsive element of the present disclosure includes an oxygen ion conductive layer, a first electrode layer having a LaSrMn-based perovskite material phase, and a second electrode layer, wherein a NOx adsorption stabilizing surface is on a surface of the first electrode layer, exposed to NOx. Therefore, the NOx decomposition efficiency is increased, and thus, the NOx detection sensitivity (responsivity) and the NOx selectivity can be improved.

Moreover, the NOx selectivity can be increased by causing the first electrode layer to be denser on the oxygen ion conductive layer side in the NOx responsive element of the present disclosure. Furthermore, the NOx decomposition efficiency and the NOx detection sensitivity can be increased by causing the particle growth of the perovskite material to be suppressed on the side exposed to NOx in the first electrode layer of the NOx sensor of the present disclosure.

According to the present disclosure, a method for producing such NOx responsive element is also provided. That is, an adsorption stabilizing surface is formed on the surface of the perovskite material, the density is controlled, and the particle growth on the surface of the perovskite material is suppressed, and thus, a NOx responsive element with high sensitivity can be produced.

Figure 1:
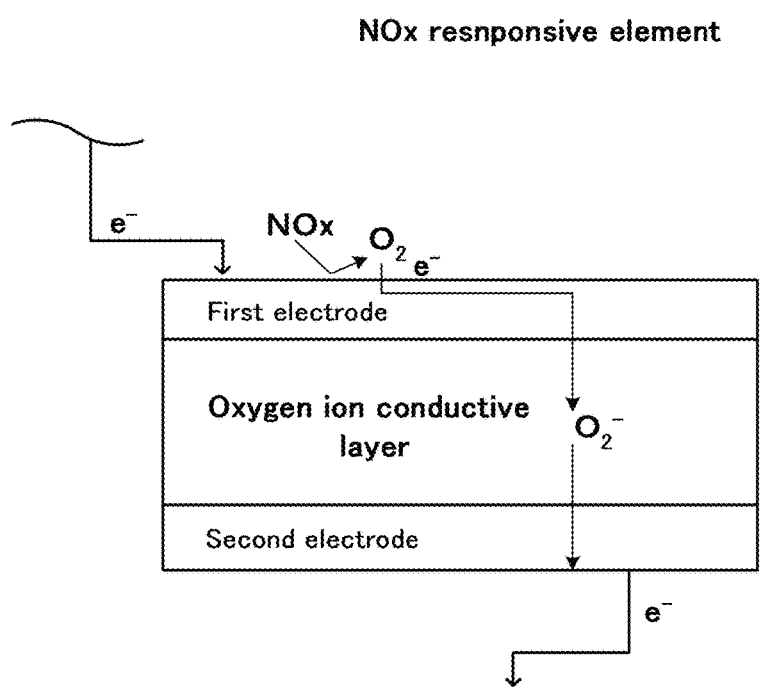
FIG. 1 is a schematic view of the NOx responsive element of the present disclosure.

FIG. 1 shows an overview of the expression of NOx responsivity in the NOx responsive element of the present disclosure (hereinafter also merely referred to as the present element). The present element can function as a current detection type sensor in which a current generated by NOx is used as a sensor signal. That is, in the present element, $O_2$ obtained by decomposing NOx in a first electrode layer with high selectivity can be further electrochemically reduced by electric power supplied to an electrochemical cell, and an oxygen ion ($O_2^-$) thus generated can be caused to move in an oxygen ion conductive layer to cause it to reach a second electrode layer. The present element read out the generated current as a sensor signal.

Figure 2:
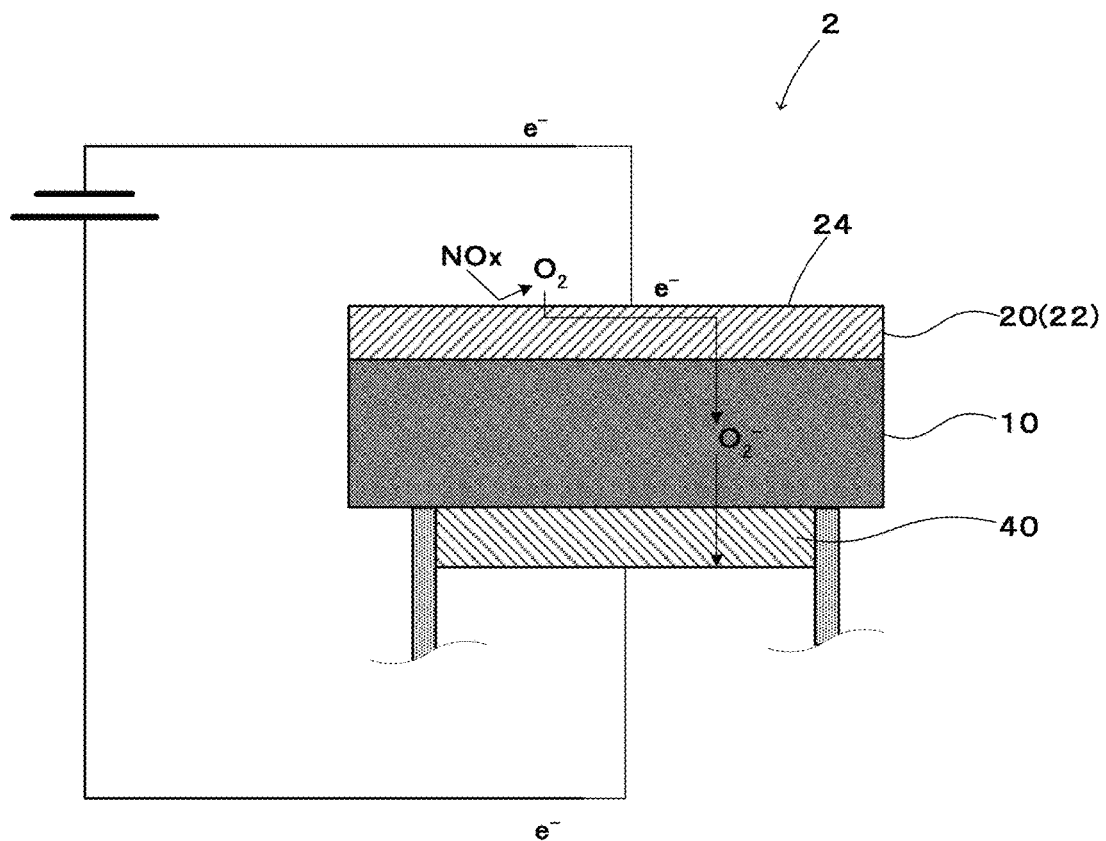
FIG. 2 is a schematic view of the NOx sensor including the NOx responsive element of the present disclosure.

Various embodiments of the present disclosure is described, as appropriate, with reference to the drawings. FIG. 2 shows an overview of an example of the present element.

(NOx responsive element) The present element 2 includes a first electrode layer 20 and a second electrode layer 40 which oppose each other across an oxygen ion conductive layer 10. Moreover, in the present element 2, a configuration of electrochemical cell in which an oxygen ion ($O_2^-$) can be moved from the first electrode layer 20 to the second electrode layer 40 can be employed.

NOx to which the present element 2 responds can be a nitrogen oxide such as nitrogen monoxide (NO), nitrogen dioxide ($NO_2$), dinitrous monoxide (dinitrogen monoxide) ($N_2O$), dinitrogen trioxide ($N_2O_3$), dinitrogen tetraoxide ($N_2O_4$), or dinitrogen pentaoxide ($N_2O_5$). In the present element 2, NOx to be decomposed is at least one of nitrogen monoxide and nitrogen dioxide, preferably both of them, among them.

NOx-containing gas to be applied to the present element 2 is only necessary to contain NOx and can, for example, be any of various combustion gases. Among them, the NOx-containing gas is preferably exhaust of various mobile bodies such as an automobile, considered as a main cause of air pollutants.

(Oxygen ion conductive layer) The oxygen ion conductive layer 20 is not limited to particular layers, and any of oxygen ion conductive materials may be used. Examples of the oxygen ion conductive material include zirconia-based solid electrolyte (typically a $ZrO_2$-$M_2O_3$ solid solution or a $ZrO_2$-MO solid solution, wherein M is preferably Y, Yb, Gd, Ca, or Mg), a ceria-based solid electrolyte (typically a $CeO_2$-$M_2O_3$ solid solution or a $CeO_2$-M solid solution, wherein M is preferably Y or Sm), a bismuth oxide-based solid electrolyte (typically $Bi_2O_3$—$WO_3$ solid solution), and $LaGaO_3$-based compound having a perovskite-type structure. From the viewpoint of the stability and the oxygen ion conductivity in the case where exhaust from internal combustion (engine) of an automobile or the like is used as NOx-containing gas, the oxygen ion conductive material is preferably a zirconia-based solid electrolyte, wherein stabilized zirconia in which 3% to 10% by mole of yttria, magnesia, or calcia relative to the total mole is dissolved is particularly preferable.

(First electrode layer) The first electrode layer 20 is in contact with (adheres to) the oxygen ion conductive layer 10 and is on the side exposed to NOx. The first electrode layer 20 functions as a decomposition electrode for decomposing NOx. The first electrode layer 20 has, on the side exposed to NOx, a NOx decomposition catalyst phase 22 (hereinafter referred to as a catalyst phase 22) composed of one or more kinds of materials having both oxygen ion conductivity and electron conductivity as well as NOx decomposition catalytic activity. It is preferred that the first electrode layer 20 is composed of only the catalyst phase 22 and does not have any coating layer on the surface layer exposed to NOx-containing gas. Such catalyst phase 22 may be composed of two or more kinds of materials and is preferably composed of one material satisfying these properties, for example.

The catalyst phase 22 may be formed of, for example, an oxygen ion conductive material, electron conductive material, and NOx decomposition catalytic active material, preferably contains perovskite-type oxide, is more preferably based on perovskite-type oxide, and is yet more preferably composed substantially of only perovskite-type oxide. The perovskite-type oxide has both of oxygen ion conductivity and electron conductivity and NOx decomposition catalytic activity. Therefore, it is considered that the above-described events occur with high NOx selectivity even at high oxygen concentration. Thus, it is considered that sufficient selective decomposition ability and sufficient response speed can be maintained even at the high oxygen concentration.

When the first electrode layer 20 has the catalyst phase 22 which contains such perovskite-type oxide, the first electrode layer 20 is exposed to NOx-containing gas, and when a voltage is applied to the present element 2, and electrons flow into the first electrode layer 20, the following events occur. It is considered that the following events are common in perovskite-type oxide.

(1) When electrons flow from an external circuit to the first electrode layer 20, the electrons diffuse in the catalyst phase 22 of the perovskite-type oxide.

(2) The catalyst phase 22 exposed to NOx-containing gas causes NOx adsorbed thereto to preferentially react with the electrons to reduce (decompose) NOx. Mixed conductive $O_2^-$ generated by this reduction diffuses in the catalyst phase 22, reaches and diffuses in the oxygen ion conductive layer 10, and reaches the second electrode layer 40.

One or more kinds of perovskite-type oxides may be used in combination. The perovskite-type oxide is represented by $ABO_3$, and A represents two or more kinds of elements selected from rare earth elements, alkali earth metal elements and alkali metal elements. Considering the formation of oxygen vacancy contributing to the decomposition function, A preferably represents one or more kinds selected from Sr, Mg, Ca, and Ba in addition to La. Considering the stability of oxygen vacancy, A is preferably selected from La, Sr, and Mg. Considering the amount of oxygen vacancy, containing two kinds of elements having different valences as A is preferable. For example, it is preferred that the percentage by mole of the element with higher valence is higher than the percentage by mole of the element with smaller valence. More preferably, in the case of perovskite-type oxide $A1pA2qBO_3$ in which A is represented by the element A1 with higher valence and the element A2 with smaller valence, p is preferably 0.6 or more to 0.8 or less, and q is preferably 0.2 or more to 0.4 or less. A1 is preferably a metal element with a valence of three and is typically La. A2 is a metal element with a valence of two and is typically Sr or Mg.

B preferably represents one or more kinds selected from the group consisting of Al, Ni, Fe, Co, Mn, Cr, and Cu. In the perovskite-type oxide having two or more kinds of elements as B, the combination of the elements is determined considering the durability, the oxygen ion conductivity, the electron conductivity, and the catalytic activity and can be preferably the combination of one or more kinds selected from Ni, Fe, Co, and Mn. B may not include Al. However, when Al is contained as the B element, the structure stability and the NOx decomposition catalytic ability at high temperature of around 750° C. under reduction atmosphere can be maintained, for example.

Examples of the perovskite-type oxide include perovskite-type oxide $La_xSr_{1-x}Co_yMn_{1-y}O_3$ ($0<x<1$, $0\leq y\leq 1$) including La—Sr—Co—O perovskite oxide, La—Sr—Mn—O perovskite oxide, La—Sr—Co—Mn—O perovskite oxide in addition to La—Sr—Ni—O perovskite oxide and La—Sr—Fe—O perovskite oxide.

In the perovskite-type oxide having two or more kinds of elements as B, the combination of the elements is determined considering the durability, the oxygen ion conductivity, the electron conductivity, and the catalytic activity, and when the combination includes Al, it is preferred that 50% or more to 100% or less by mole of Al is contained. The combination of one or more kinds of elements besides Al is preferably Co and Mn from the viewpoint of the catalytic activity. In this case, as to Al, the percentage by mole (y) to be contained is preferably 60% or more to less than 100% by mole, and the total percentage by mole (1−y) of the remaining element is preferably 0% or more to 40% or less by mole.

Such perovskite-type oxide typically can be perovskite-type oxide $La_xSr_{1-x}Al_yC_{1-y}O_3$ (C represents one or more kinds selected from the group consisting of Ni, Fe, Co, Mn, Cr, Cu, Rh, and V, $0<x<1$, $0<y\leq 1$) including La—Sr—Al—C—O perovskite oxide which includes La—Sr—Al—O perovskite-type oxide. In this perovskite-type oxide $La_xSr_{1-x}Al_yC_{1-y}O_3$, $0.6\leq x\leq 0.8$, preferably $0.6\leq y\leq 1$, and more preferably $0.6\leq y\leq 0.8$.

The first electrode layer 20 may contain a noble metal such as palladium (Pd), platinum (Pt), or rhodium (Rh) in the range in which selective NOx decomposition ability of the catalyst phase 22 is not impaired.

(NOx adsorption stabilizing surface) The present element 2 has a NOx adsorption stabilizing surface 24 on a surface of the catalyst phase 22, exposed to NOx. As mentioned above, the decomposition of NOx in the catalyst phase 22 is based on the adsorption of NOx to the catalyst phase 22. Therefore, the NOx decomposition efficiency and the NOx selectivity (of $O_2$) are improved by including the adsorption stabilizing surface 24.

The NOx adsorption stabilizing surface 24 is set according to the materials composing the catalyst phase 22. The adsorption stabilizing surface 24 is selected from a plurality of termination surfaces included in crystal structures of materials for composing the catalyst phase 22. The adsorption stabilizing surface 24 can be experimentally selected. For example, the catalyst phase 22 may be synthesized so as to expose different termination surfaces on the surface layer of the catalyst phase 22 to compose the first electrode layer 20, an adsorption desorption test (temperature programmed desorption (TPD)) of NOx and $O_2$ may be performed, and an termination surface which can most stabilize the adsorption of NOx may be selected according to the desorption state of molecule and the like. Furthermore, the present element 2 may be configured as a whole, and the NOx responsive sensitivity and the NOx selectivity may be evaluated, and an termination surface which can most stabilize the adsorption of NOx may be selected. Moreover, TPD may be performed using the first-principles calculation, and an termination surface whose adsorption energy (energy obtained (or lost) by adsorption of gas on the surface) at the time of adsorption of NOx is low, may be selected.

In the case of using the first-principles calculation, an electron state calculation package VASP (VASP (abbreviation for Vienna Ab initio Simulation Package (http://www.vasp.at/)), G. Kresse and D. Joubert. "From ultrasoft pseudopotentials to the projector augmented-wave method" Phys. Rev. B, 59:1758 (1999)) (software for commercial use, developed by Prof. J. Hafner (University of Vienna) et al.) based on the density functional theory may be used.

As a method, a calculation method based on a PAW method of plane wave basis (PAW (abbreviation for projector augmented wave) method is a method for handling core electrons which do not significantly contribute to the interatomic bond, developed by Blöchl, P. E. Blöchl, "Projector augmented-wave method", Phys. Rev. B 50, 17953 (1994).) is used, for calculation of exchange-correlation interaction of electrons, PBE-GGA (abbreviation for Perdew-Burke-Ernzerh of generalized gradient approximation, PBE generalized-gradient approximation) which is an approximate method for handling interelectronic interaction in a framework of quantum mechanics, developed by Perdew et al., Perdew, J. P.; Burke, K.; Ernzerhof, M. "Generalized Gradient Approximation Made Simple". Phys. Rev. Lett. 77, 3865 (1996).) is used, and for d orbit of Mn at the plane-wave cutoff energy of 500 eV, a DFT+U method (DFT+U method is a method for correcting interaction of d-orbital electrons of Mn which cannot be expressed by PBE-GGA, S. L. Dudarev, G. A. Botton, S. Y. Savrasov, C. J. Humphreys, A. P. Sutton, "Electron-energy-loss spectra and the structural stability of nickel oxide: An LSDA+U study", Phys. Rev. B 57, 1505 (1998)) is used (U=3.4 eV).

In order to determine a stable structure (energy), structural optimization was performed until the force on electrons is converged to 0.01 eV/Å or less using a structural optimization algorithm by a conjugate gradient method. The conjugate gradient method is a method for searching for the minimum of energy. In order to minimize energy, it is required to repeatedly perform a step of firstly calculating force on each electron and secondarily moving electrons in a direction in which the energy becomes zero. In the conjugate gradient method, not only the information on the force in the focused step, but also the information on the force in the previous step are utilized to determine the direction in which the electrons are moved, and thus, the energy can be minimized at high speed.

In the first-principles calculation, a bulk model for searching for an adsorption stabilizing surface is selected. The case where perovskite-type oxide $La_{0.75}Sr_{0.25}MnO_3$ is used as a bulk model is described below.

From the bulk model, for example, surface models to be compared such as (001) surface models of two types of the $MnO_2$ termination surface and the LaO termination surface were cut out and prepared. In this example, as the surface models, five slab electron layers are used, and the size of the surface corresponding to $2\sqrt{2} \times 2\sqrt{2}$ (8 times) of cubic perovskite (001) surface may be used.

The adsorption selectivity is checked by comparing the adsorption energy of NO molecule and that of $O_2$ molecule with respect to the bulk model. The temperature of adsorption energy and the gas partial pressure of each of NO and O2 may be calculated from Linstrom P J, Mallard W G (Eds.). NIST Chemistry WebBook, NIST Standard Reference Database Number 69, National Institute of Standards and Technology, http://webbook.nist.gov, (retrieved Jul. 7, 2013), which is a thermodynamic database published in JANAF-NIST Thermochemical Tables (NIST-JANAF Thermochemical Tables: (NIST is abbreviation for National Institute of Standards and Technology (US)). The gas partial pressure can be set as appropriate and can be calculated at $O_2$=0.2 atm and NO=$10^{-3}$ atm (corresponding to 1000 ppm) or less based on the simulation of $O_2$ gas partial pressure in atmosphere, for example.

For example, when NO and $O_2$ on the surface models of the above-described perovskite-type oxide were calculated, the results showed that, in the temperature range of T<1000° C., the adsorption of NO selectively easily occurs on the $MnO_2$ termination surface, whereas the adsorption of NO does not easily occur on the LaO termination surface compared with the adsorption of $O_2$.

As described above, the adsorption stabilizing surface 24 of the catalyst phase 22 composed of LaSrMn-based perovskite-type oxide can be the $MnO_2$ surface. As to other perovskite-type oxides, the adsorption stabilizing surface 24 of the catalyst phase 22 can be similarly determined experimentally or by the first-principles calculation.

The adsorption stabilizing surface 24 with specific composition can be determined by, for example, the X-ray electron spectrometry (XPS).

The catalyst phase 22 having such adsorption stabilizing surface 24 can be obtained by synthesizing the catalyst phase 22 under the firing conditions under which the termination surface with specific composition is obtained by the findings and experiments of the surface structures of known ceramics. For example, in the case of LaMnO-based perovskite-type oxide, conditions under which the $MnO_2$ termination surface is easily obtained can be understood based on the document (S. Piskunov et al., "Electronic structure and thermodynamic stability of $LaMnO_3$ and $LaSrMnO_3$ (001) surfaces: Ab initio calculations", Phys. Rev. B78, 12406(R) (2008)) or the like. That is, in the case of LaMnO-based perovskite-type oxide, the $MnO_2$ termination surface can be more easily obtained by firing under the conditions of 0.01 atmospheres or more to 1 atmosphere or less of oxygen partial pressure and 530° C. or more to 1300° C. or less. The temperature is more preferably 750° C. or more to 1100° C. or less, yet more preferably 800° C. or more to 1000° C. or less. The oxygen partial pressure is more preferably 0.1 atmospheres or more, yet more preferably 0.2 atmospheres or more which is the atmospheric condition.

In order to form the catalyst phase 22 of perovskite-type oxide or the first electrode layer 20 as a thin film (with a thickness of about 1000 nm or less) under the firing conditions, the following method can be employed, for example. That is, an aqueous solution of each salt (a salt of organic acid such as acetate or propionate, a salt of inorganic acid such as a salt of nitric acid, or the like) of components such as La, Sr, Mn and the like is prepared, a film is formed on an oxygen ion conductive layer by spin coating or the like of the aqueous solution, and the film is fired to synthesize a ceramic film. At that time, in order to maintain the uniformity and the density of the film, it is preferred that aggregation of particles is suppressed by adding an appropriate stabilizing agent. Such stabilizing agent is not limited to particular agents, and amino ethanol or acetoin is preferably used. As an aqueous medium, 2-ethoxyethanol or the like is preferably used.

The catalyst phase 22 of the perovskite-type oxide can be obtained by performing a film forming step of applying a raw material solution on an oxygen ion conductive layer 10 (or a material layer thereof) and drying it (for example, at about 500° C.) and thereafter performing a firing step under the above-mentioned firing conditions. It is preferred that the film forming step is performed one or more times, as appropriate, and the firing step is thereafter performed. A set of a step of forming a catalyst phase including the film forming step and the firing step is performed one or more times, preferably three or more times, to the extent that the required density and the required film thickness are obtained.

It is preferred that the catalyst phase 22 is uniformly dense as a whole, and it is preferred that the catalyst phase 22 is denser on the oxygen ion conductive layer 10 side and is less dense (i.e., highly porous) on the exposed side. Accordingly, the oxygen responsivity is reduced, and thus, the NOx selective responsivity can be increased. As to causing the catalyst phase 22 to be uniformly dense and gradually increasing the density toward the oxygen ion conductive layer 10 side, for example, supplying the above-described raw material solution to the oxygen ion conductive layer 10 to form a film and thereafter firing the film are performed a plurality of times, and thus, perovskite-type oxide is synthesized and sintered in each film, and therefore, the density can be increased and can be uniform as a whole. Moreover, on the oxygen ion conductive layer 10 side, the number of times of firing and the density are more increased.

The gradual increase of the density in the catalyst phase 22 can be determined by measuring the porosity in the cross section of the catalyst phase 22 or the like with an electron microscope photograph or the like.

It is preferred that the particle growth of the perovskite-type oxide is suppressed on the side exposed to NOx in the catalyst phase 22. Accordingly, the specific surface area of the catalyst phase 22 can be increased on the exposed surface side. In other words, the specific surface area or the porosity is preferably high on the side exposed to NOx in the catalyst phase 22. Accordingly, the increase in oxygen responsivity can be suppressed, the NOx responsivity can be increased, and thus, the NOx responsivity and the NOx selectivity can be improved.

The suppression of particle growth of the perovskite-type oxide on the side exposed to NOx can be determined by observing the cross section or the like of the catalyst phase 22 with an electron microscope or the like, for example.

The suppression of the particle growth of the perovskite-type oxide on the side exposed to NOx in the catalyst phase 22 can be achieved by firing a raw material solution at low temperature within the above-described firing conditions. Specifically, the firing is performed at preferably 700° C. or more to 900° C. or less, and more preferably around 750° C. or more to 850° C. or less.

As described above, the surface exposed to NOx in the catalyst phase 22 of the first electrode layer 20 in the present element 2 has a NOx adsorption stabilizing surface 24, the particle growth of the perovskite-type oxide is suppressed on the side exposed to NOx in the catalyst phase 22, and the catalyst phase 22 is denser on the oxygen ion conductive layer 40 side.

(Second electrode layer) The second electrode layer 40 is in contact with (closely adheres to) the oxygen ion conductive layer 10 so as to oppose the first electrode layer 20 across the oxygen ion conductive layer 10. The second electrode layer 40 is a counter electrode of the first electrode layer 10 which is a decomposition electrode and functions as a standard electrode or a reference electrode. The second electrode layer 40 is only required to have electron conductivity, and the material for composing the second electrode layer 40 is not limited to particular materials. Examples of an electron conductive material include noble metals belonging to platinoid element (typically Pt, Pd, and Rh), noble metals other than those belonging to platinoid element (typically Au and Ag), and base metals having high conductivity (for example, Ni). Examples of the electron conductive material further include alloys based on any of the metals (for example, Pt—Rh and Pt—Ir). Examples of the electron conductive material further include metal oxides such as nickel oxide, cobalt oxide, copper oxide, lanthanum manganite, lanthanum cobaltite, and lanthanum cobaltite. The second electrode layer 40 can contain one or more kinds of these electron conductive materials. Moreover, the second electrode layer 40 may contain an oxygen ion conductive material. As the oxygen ion conductive material, the same material used in the oxygen ion conductive layer 10 may be used. Examples of the oxygen ion conductive material include zirconia stabilized by yttria or scandium oxide, ceria stabilized by gadolinium oxide or samarium oxide, and lanthanum gallate. Considering the balance with the electron conductivity of the second electrode layer 40 and the adhesiveness to the oxygen ion conductive layer 10 and the like, the second electrode layer 40 contains the oxygen ion conductive material preferably in the range of 0% or more to 10% or less by mass, and more preferably 1% or more to 5% or less by mass, relative to the total mass of the second electrode layer 40.

(Method for producing NOx responsive element) The present element described above can be generally produced by a general method. That is, the method for producing the present element can include a step of forming an oxygen ion conductive layer composed of an oxygen ion conductive material and a step of forming a first electrode layer having a catalyst phase composed of a perovskite-type oxide material on the oxygen ion conductive layer. The second electrode layer may be formed on the oxygen ion conductive phase in advance or may be provided after forming the first electrode layer. Firing of the oxygen ion conductive layer, the first electrode layer, and the second electrode layer can be performed as appropriate if necessary.

In the present production method, in order to obtain the present element, the step of forming a first electrode layer is performed so as to form an adsorption stabilizing surface on the surface of the catalyst phase. As the adsorption stabilizing surface and the method for forming the same, those mentioned for the form of the present element can be applied. Therefore, in the case of forming a catalyst phase by firing raw materials of the LaSrMn-based perovskite material, $MnO_2$ can be formed.

It is preferred that the step of forming a first electrode layer is performed so that the catalyst phase is denser on the oxygen ion conductive layer side. As to the advantages of providing such density in the catalyst phase and the method for forming the catalyst phase, those described for the form of the present element can be applied.

Furthermore, it is preferred that the step of forming a first electrode layer is performed so that the particle growth of the perovskite-type oxide material is suppressed on the side exposed to NOx in the catalyst phase. As to the advantages of providing such form of particle growth in the catalyst phase and a method for forming the catalyst phase, those described for the form of the present element can be applied.

(NOx sensor) According to the present disclosure, a NOx sensor including the present element is also provided. The present NOx sensor is configured so that a voltage can be applied to the present element. The present NOx sensor may further include a current detection unit of detecting a current detected by the NOx sensor or may further include a control unit which can calculate the NOx concentration based on a current detected through the contact with NOx-containing gas.

It is preferred that the present NOx sensor is configured so that the catalyst phase 22 of the first electrode layer 10 is directly exposed to NOx-containing gas, and the second electrode layer 40 is in the state where the first electrode layer 20 is shielded or can be shielded from the NOx-containing gas to which the first electrode layer 20 is exposed. It is preferred that a material having sufficient insulation properties and sufficient heat resistance in the temperature range in which the NOx sensor is used is used as the partition for shielding the second electrode layer 40 from the NOx-containing gas. Examples of the material include ceramic materials such as alumina, magnesia, mullite, and cordierite.

The present NOx sensor can include a temperature control unit of controlling the temperature of the present element. By including the temperature control unit, the ion conductivity of the oxygen ion conductive layer 10 and the NOx (for example $NO_2$) selectivity of $O_2$ can be adjusted as appropriate. The temperature control unit can include, for example, a heating (or cooling) unit for heating or cooling the present element or the vicinity thereof or both of them, a temperature sensor for detecting the temperature of the present element or the vicinity thereof, and a control circuit which outputs a control signal for controlling the temperature of the present element or the like based on the signal from the temperature sensor.

The temperature control unit is not limited to particular units, and any of various known units may be used. The temperature control by the temperature control unit is only required to decompose NOx and is not particularly limited. An electrochemical cell 10 of the NOx decomposition device 2 of the present teaching can be stably operated at 400° C. or more to 800° C. or less. Considering the NOx selectivity, the electrochemical cell 10 controls the temperature of the electrochemical cell 10 or the vicinity thereof to preferably 750° C. or less, more preferably 700° C. or less, and yet more preferably 600° C. or less. When the temperature is controlled to 600° C. or less, the NOx selectivity can be 70% or more. Considering the NOx selectivity, the temperature is more preferably 550° C. or less. On the other hand, considering the ion conductivity of the oxygen ion conductive layer 10, the temperature is controlled to preferably 450° C. or more, and more preferably 500° C. or more. The temperature preferred in the present element is 450° C. or more to 700° C. or less, more preferably 450° C. or more to 650° C. or less, and yet more preferably 500° C. or more to 600° C. or less.

As the present NOx sensor, any of various NOx sensing forms can be employed. Typically, the present NOx sensor can be in a form (direct sensing type) of, under the atmosphere of the temperature to the extent that the oxygen ion conductivity of the oxygen ion conductive layer 10 is exerted, applying a voltage to the first electrode layer 20 and the second electrode layer 40, exposing the first electrode layer 10 to NOx-containing gas, and directly decomposing NOx in the NOx-containing to sense NOx. The present element selectively decomposes NOx at high oxygen concentration and has high NOx sensitivity. Thus, the present element can sense NOx in NOx-containing gas whose oxygen concentration is not controlled in the predetermined range in advance. The oxygen concentration of the NOx-containing gas which can be applied to the present NOx sensor is not limited to particular concentrations and is preferably 0.5% or more, more preferably 1% or more, yet more preferably 5% or more, still more preferably 10% or more, and even more preferably 15% or more. The upper limit is not limited to particular concentrations and is preferably 21% or less which is the oxygen concentration in atmosphere.

On the other hand, the NOx concentration of the NOx-containing gas to which the catalyst phase is exposed, i.e., the total concentration of one or more kinds of various nitrogen oxide gases may be 1000 ppm or less, and is preferably at least 10 ppm or more.

At the time of sensing NOx, a voltage to be applied to the present element is, specifically, applied from an external circuit so as to supply electrons to the first electrode layer 20. The magnitude (absolute value) of the voltage to be applied is not limited to particular magnitudes and may be, for example, about 1 V or less, and more preferably 100 mV or less.

The present NOx sensor can stably maintain the structure of the perovskite-type oxide in the catalyst phase 22, can exert NOx selective decomposition ability, and can sense NOx, under reduction atmosphere. The reduction atmosphere refers to the atmosphere based on reducing gas. Examples of the reducing gas include $SO_2$, $H_2S$, CO, NO, and CO. The reduction atmosphere can be typically atmosphere based on carbon monoxide (CO) and hydrocarbons (HCs). The present NOx sensor can stably maintain the structure even under the reduction atmosphere at higher temperature of around 800° C. Such reduction atmosphere is an environment which can be generated in an engine of a mobile body such as automobile, for example. Moreover, such reduction atmosphere is prone to be generated in the state where the air-fuel ratio is fuel rich. Therefore, the present NOx sensor can be preferably applied to NOx sensor for exhaust of engines of various mobile bodies and the like.

The present NOx sensor includes the present element for decomposing and detecting NOx and thus can be utilized as a NOx decomposition device.

(Method for sensing NOx by NOx sensor) According to the present disclosure, a method for sensing NOx by the present NOx sensor is also provided. The present method for sensing may include the sensing step of exposing the present NOx sensor to NOx-containing gas to sense NOx. The present sensing step can be performed in various forms of the NOx sensor described above. The present method for sensing may also be performed as a method for decomposing NOx.

EXAMPLE

The present teaching is described in detail below with reference to an example. The present teaching, however, is not limited by the following example.

Example 1

In the following example, a NOx responsive element and a direct decomposition-type NOx sensor were produced. NOx was decomposed and measured using the produced NOx sensor under the following conditions. That is, an element using perovskite-type oxide as a catalyst phase of a first electrode layer was produced and introduced into a glass tube with an electric furnace, gas shown in the following was circulated into the element, a voltage was applied so as to produce an electric potential difference between a decomposition electrode and a counter electrode using potentiostat, and a current was read out. The element was produced as follows.

(1) Production of oxygen ion conductive layer (YSZ pellet) A YSZ powder (zirconia in which 8% by mole of $Y_2O_3$ was dissolved, produced by Tosoh Corporation) was subjected to uniaxial pressing using a tablet forming machine with a diameter of 10 mm, was thereafter subjected to cold isostatic pressing (CIP), and was fired at 1530° C. for 2 hours under air atmosphere. Thus, a pellet with a diameter of about 9 mm and a thickness of 1 mm was produced.

(2) Production of first electrode layer (decomposition electrode) and second electrode layer (counter electrode) Subsequently, a raw material solution in which the equimolecular amounts of $La(NO_3).6H_2O$, $Mn(COOH)_2.4H_2O$, and $Sr(O(C_3H_7)_2))$ to LaSrMn-based perovskite-type oxide were contained, ethanol amine and acetoin were used as dispersants, and 2-methoxymethanol was used as a solvent was prepared. In the raw material solution, La: 0.08 mol/l, Sr: 0.02 mol/l, Mn: 0.1 mol/l, ethanol amine: 0.2 mol/l, and acetoin: 0.1 mol/l. Each inorganic raw material was dissolved in methoxyethanol, and thereafter ethanol amine and acetoin were added to prepare the raw material solution.

Figure 7:
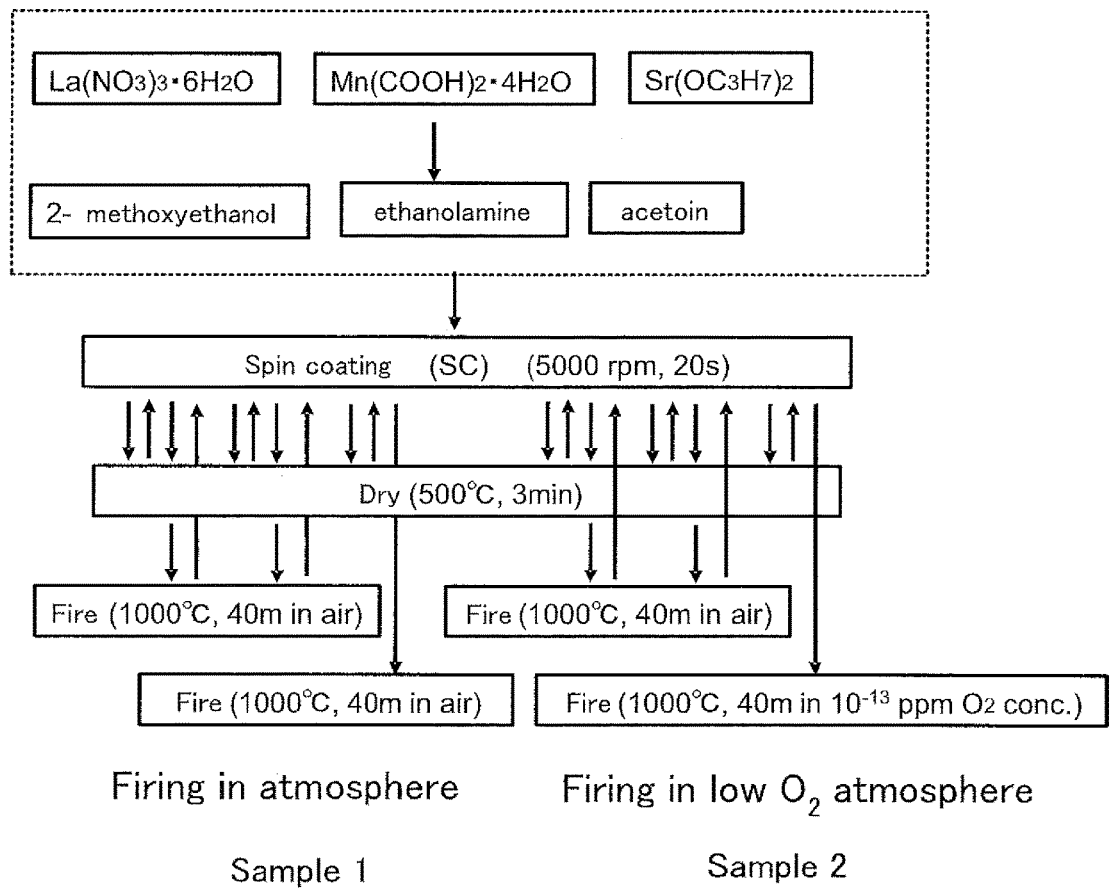
FIG. 7 is a flow chart of preparation of samples 1 and 2 in the example.
Figure 8:
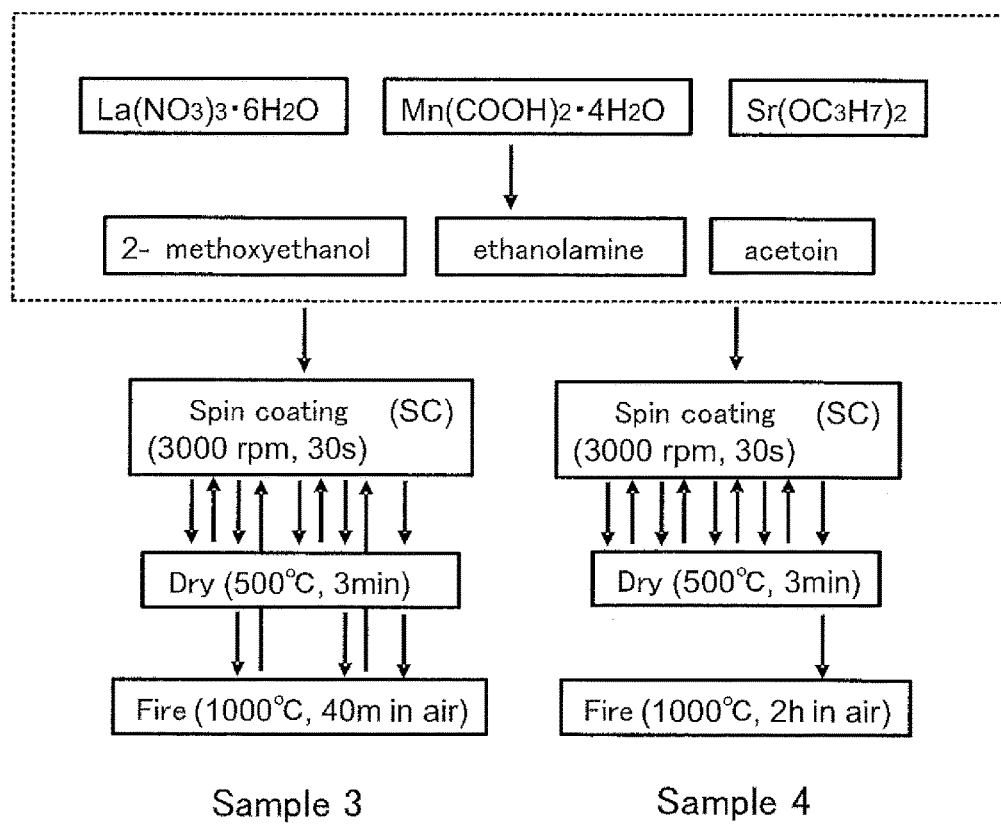
FIG. 8 is a flow chart of preparation of samples 3 and 4 in the example.
Figure 9:
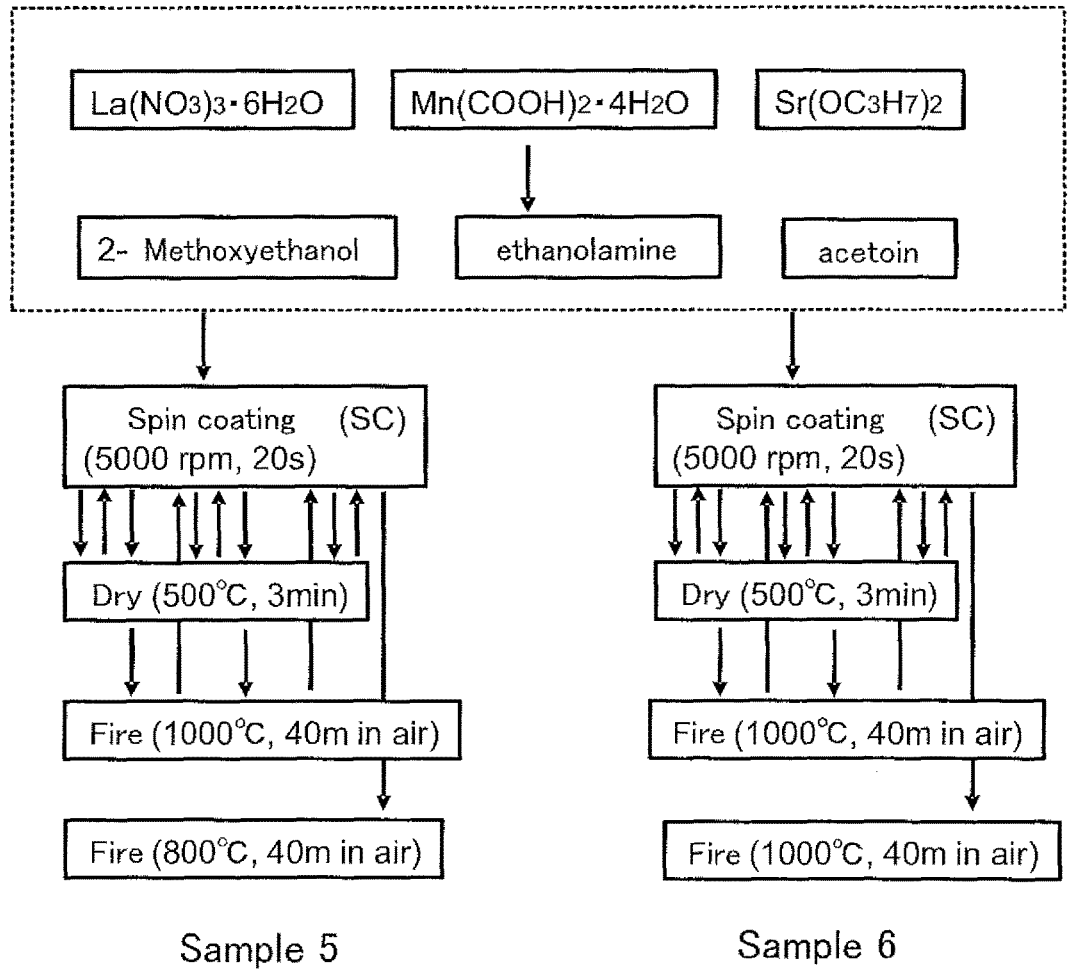
FIG. 9 is a flow chart of preparation of samples 5 and 6 in the example.

This raw material solution was applied to a surface of the produced YSZ pellet by spin coating under the conditions disclosed in FIGS. 7 to 9, then dried and fired. Furthermore, a platinum paste (TR7095, produced by Tanaka Kikinzoku Kogyo) was printed on the opposite surface of the YSZ pellet using a screen with a diameter of 3 mm. Thus, various element samples were produced. The thickness of each catalyst phase was 50 to 500 nm, and the contact between the YSZ pellet and the NOx-containing gas could be shielded.

(3) Attachment of electric collector A Pt needle of Pt paste (TR7905, produced by Tanaka Kikinzoku Kogyo) was joined to the surface of the decomposition electrode of the obtained element so as to be in a form shown in FIG. 2 and was baked at 1000° C. for 2 hours in atmosphere. Thus, an electric collector and a lead wire were fixed.

(4) Attachment of magnesia tube As a partition for pertitioning the decomposition electrode and the counter electrode with respect to NOx-containing gas, a magnesia tube (MgO, outer diameter×inner diameter×length=6 mm×4 mm×350 mm) was used. The magnesia tube was joined to an electrochemical cell using an inorganic adhesive so as to expose the sensing electrode and the counter electrode to different gas atmospheres in a form shown in FIG. 2. Thus, a direct decomposition-type NOx decomposition device was obtained.

(5) Provision of NOx-containing gas Base gas and NOx-containing gas were provided. The base gas was synthesized air having simulated air composition, and the NOx-containing gas was prepared by diluting 500 ppm of $NO_2$ with the base gas. These gases were provided by using gas cylinders of pure oxygen ($O_2$), pure nitrogen ($N_2$), and 1000 ppm of nitrogen dioxide ($NO_2$, a mixed gas of 1000 ppm (0.1%) of pure nitrogen and $NO_2$) and adjusting the concentration through controlling the flow rate of each cylinder.

Figure 3:
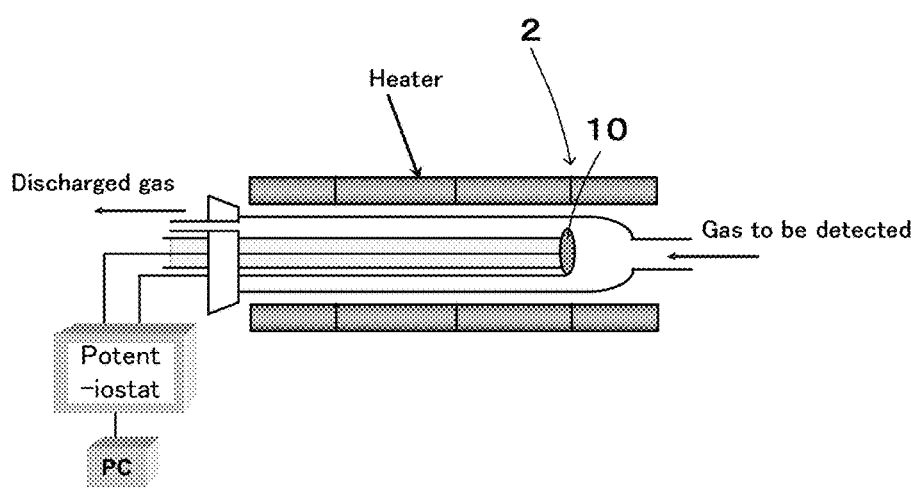
FIG. 3 is a drawing showing a form of sensing NOx using the NOx sensor of the present disclosure.

(6) Measurement method The produced element was introduced into a glass tube with a flange so as to be in a form shown, as an example, in FIG. 3, the base gas was flowed into the glass tube, NOx-containing gas was thereafter circulated in the glass tube, in order to circulate the gases, a voltage was applied so as to produce an electric potential difference between the decomposition electrode and the counter electrode using potentiostat, and a current was read out. The circulation of gases was performed using a heater in the state where the temperature was increased to 500° C. or 600° C., and the flow rate was 100 cm$^3$/min by a mass flow meter, and the electric potential difference produced by applying a voltage was 0 to 50 mV.

Figure 4:
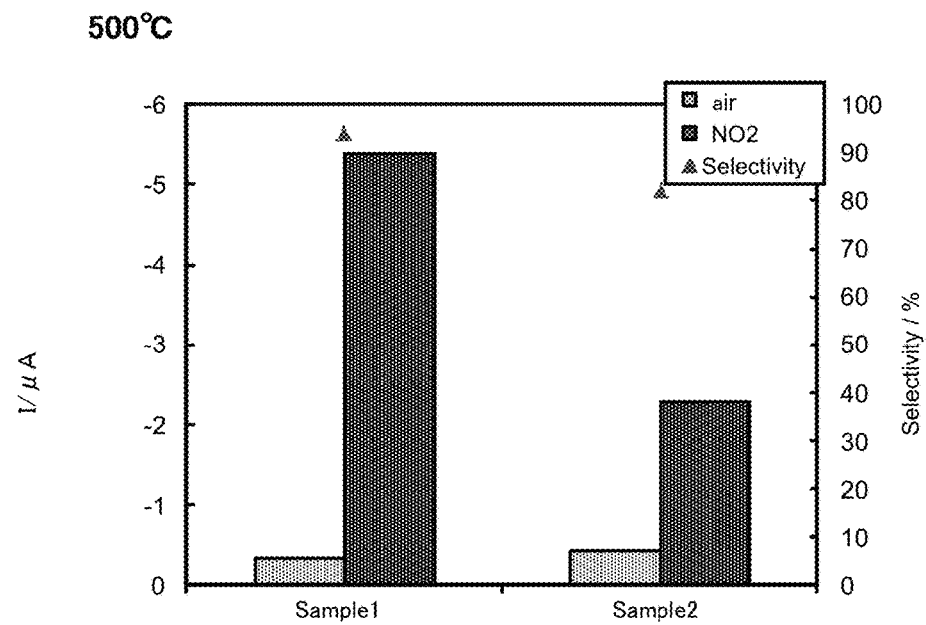
FIG. 4 is a graph showing NOx measurement results in the example.
Figure 4:
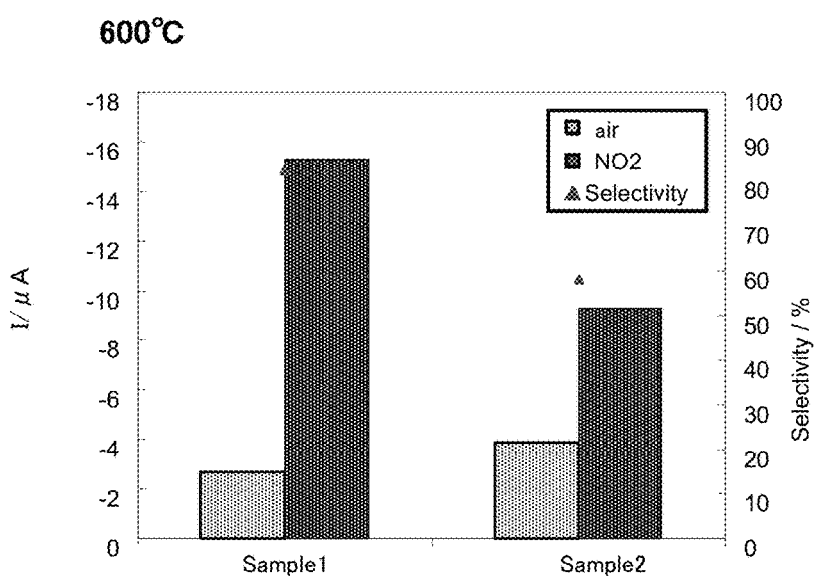
Figure 5:
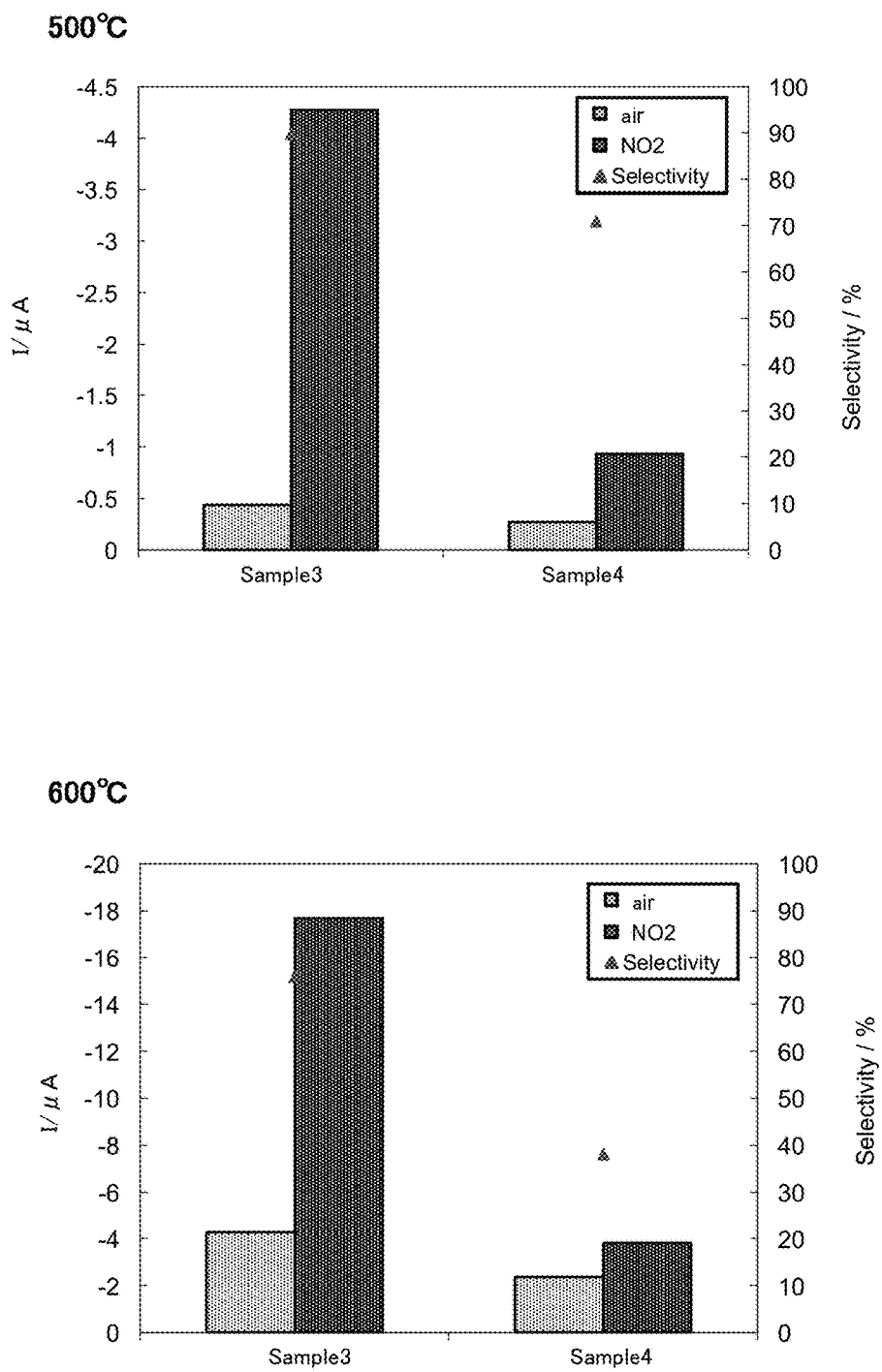
FIG. 5 is a graph showing NOx measurement results in the example.
Figure 6:
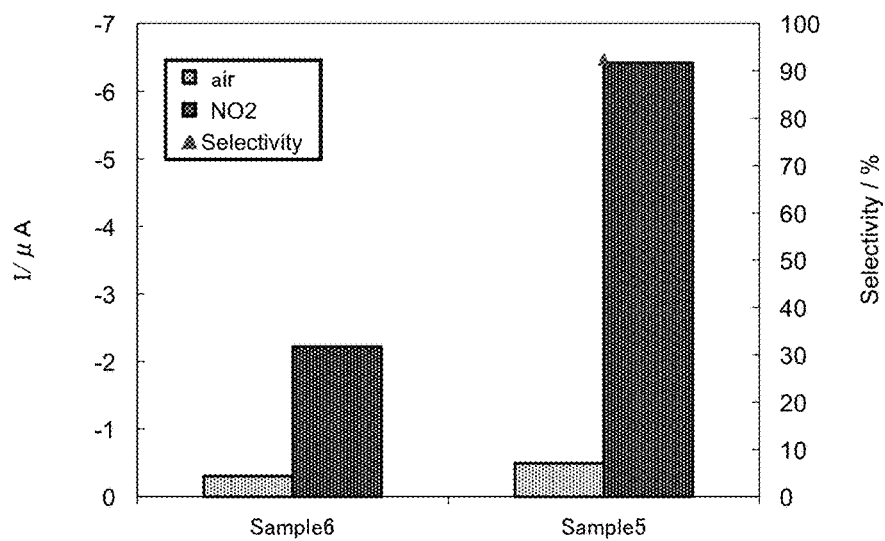
FIG. 6 is a graph showing NOx measurement results in the example.
Figure 6:
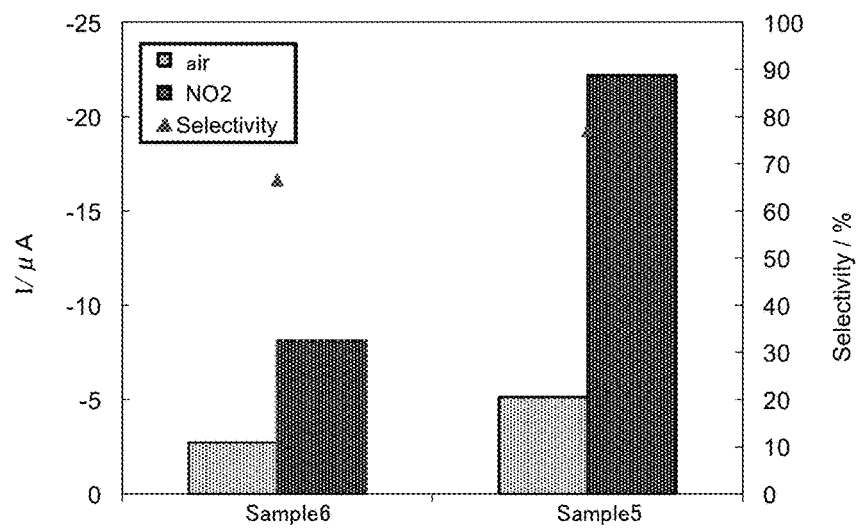

(7) Results The results are shown in FIGS. 4 to 6. As shown in FIG. 4, as to both of sample 1 (in the case of firing in atmosphere) and sample 2 (in the case of firing in low $O_2$ atmosphere), sample fired in atmosphere showed high NOx sensitivity and high NOx selectivity at any operation temperature. The conditions where firing is performed in atmosphere are conditions where the termination surface of LaSrMn becomes $MnO_2$, and the conditions where firing is performed in low $O_2$ atmosphere are conditions where LaO surface becomes an termination surface. The difference in termination surface caused by the difference in these conditions could be determined by XPS. The above results demonstrated that when the $MnO_2$ was an termination surface, favorable NOx sensitivity and favorable NOx selectivity could be obtained. Moreover, it was determined that the oxygen rich conditions such as the conditions where firing was performed in atmosphere were preferable for forming the $MnO_2$ surface.

Moreover, as shown in FIG. 5, comparing sample 3 (firing a plurality of times) and sample 4 (firing one time) demonstrated that the NOx sensitivity and the NOx selectivity were superior in the case of the conditions where firing is performed a plurality of times. Comparing the decomposition electrode and the cross section of sample 3 and those of sample 4 by observation with an electron microscope demonstrated that sample 3 was denser on the YSZ side. As described above, it was demonstrated that when the density is higher on the oxygen ion conductive side, the NOx sensitivity and the NOx selectivity were improved.

Moreover, as shown in FIG. 6, comparing sample 5 (the final firing was performed at 800° C. in three-time firing) and sample 6 (three-time firing was performed at 1000° C.) demonstrated that the NOx sensitivity and the NOx selectivity were superior in the case where the final firing was performed at 800° C. Comparing the decomposition electrode and the cross section of sample 5 and those of sample 6 by observation with an electron microscope demonstrated that sample 5 was denser on the YSZ side of LaSrMn of the side exposed to NOx gas. As described above, it was demonstrated that when the density is higher on the oxygen ion conductive layer side, the NOx sensitivity and the NOx selectivity were improved.

When the NOx-containing gas was supplied, the NOx decomposition current was about 10 times higher than the current at the time of supplying the base gas, and the electric power consumption efficiency showed 93.4%. Moreover, it was demonstrated that, according to the above-described conditions and the obtained current, the decomposition current of 5 µA was obtained. These NOx decomposition conditions and results were applied to the case where typical exhaust (2000 cc-engine, 2 m$^3$/min, 500 ppm of NO) was decomposed with an electrochemical cell with 500 cm$^2$ of electrode area, and the NOx decomposition efficiency was calculated. The result demonstrated that the electrochemical cell of the present teaching could decompose and purify 98.8% of NO in the typical exhaust.

The example demonstrates that, according to the NOx decomposition device of the present teaching, even in the presence of the largely excess amount of oxygen, the influence thereof can be suppressed, and NOx can be selectively decomposed with high electric power using efficiency.

What is claimed is:

1. A nitrogen oxide responsive element comprising:
   an oxygen ion conductive layer;
   a first electrode layer having a nitrogen oxide decomposition catalyst phase composed of perovskite-type oxide, being in contact with the oxygen ion conductive layer, and being exposed to NOx, and
   a second electrode layer opposing the first electrode layer across the oxygen ion conductive layer,
   wherein
   the nitrogen oxide decomposition catalyst phase has a surface exposed to nitrogen oxide and the surface includes a nitrogen oxide adsorption stabilizing surface,
   the perovskite-type oxide is LaSrMn-based perovskite oxide,
   the surface has an $MnO_2$ termination surface mainly as the nitrogen oxide adsorption stabilizing surface,
   the first electrode layer is denser on a side of the oxygen ion conductive layer, and
   particle growth of the perovskite-type oxide is suppressed more on a side exposed to nitrogen oxide of the first electrode layer.

2. A nitrogen oxide sensor comprising the element according to claim 1.

3. A method for producing the nitrogen oxide responsive element according to claim 1, comprising:
   forming the first electrode layer having the nitrogen oxide decomposition catalyst phase composed of perovskite-type oxide on a layer composed of an oxygen ion conductive material,
   wherein forming the first electrode layer includes firing a raw material of LaSrMn-based perovskite-type oxide under oxygen rich atmosphere to form the first electrode layer,
   wherein the first electrode layer forming is performed so as to form an $MnO_2$ termination surface mainly as the NOx adsorption stabilizing surface on the surface exposed to nitrogen oxide, and
   wherein the first electrode layer forming step includes forming the first electrode layer so that particle growth of the perovskite-type oxide is suppressed more on the surface exposed to nitrogen oxide.

* * * * *